US011779233B2

(12) United States Patent
Huo et al.

(10) Patent No.: US 11,779,233 B2
(45) Date of Patent: Oct. 10, 2023

(54) METHOD FOR CALCULATING FRACTIONAL FLOW RESERVE BASED ON PRESSURE SENSOR AND ANGIOGRAPHIC IMAGE

(71) Applicant: SUZHOU RAINMED MEDICAL TECHNOLOGY CO., LTD., Jiangsu (CN)

(72) Inventors: Yunfei Huo, Jiangsu (CN); Guangzhi Liu, Jiangsu (CN); Xingyun Wu, Jiangsu (CN)

(73) Assignee: SUZHOU RAINMED MEDICAL TECHNOLOGY CO., LTD., Suzhou (CN)

( * ) Notice: Subject to any disclaimer, the term of this patent is extended or adjusted under 35 U.S.C. 154(b) by 363 days.

(21) Appl. No.: 17/132,689

(22) Filed: Dec. 23, 2020

(65) Prior Publication Data

US 2021/0113100 A1     Apr. 22, 2021

Related U.S. Application Data

(63) Continuation of application No. PCT/CN2019/086610, filed on May 13, 2019.

(30) Foreign Application Priority Data

Mar. 19, 2019   (CN) .......................... 201910206438.8

(51) Int. Cl.
*G06T 7/11*     (2017.01)
*A61B 5/02*     (2006.01)
(Continued)

(52) U.S. Cl.
CPC ........ *A61B 5/0275* (2013.01); *A61B 5/02007* (2013.01); *A61B 5/0215* (2013.01);
(Continued)

(58) Field of Classification Search
CPC . A61B 5/02007; A61B 5/0215; A61B 5/0275; A61B 5/504; A61B 5/6852;
(Continued)

(56) References Cited

U.S. PATENT DOCUMENTS 10,052,158 B2    8/2018   Taylor
10,111,633 B2 *  10/2018  Nickisch ................ A61B 6/463
(Continued)

FOREIGN PATENT DOCUMENTS

CN    104582572    4/2015
CN    105326486    2/2016
(Continued)

OTHER PUBLICATIONS

Siogkas et al., "Computational Assessment of the Fractional Flow Reserve from Intravascular Ultrasound and Coronary Angiography Data: a Pilot Study", 35th Annual International Conference of the IEEE EMBS, Jul. 3-7, 2013, pp. 3885-3888 (Year: 2013).*

(Continued)

*Primary Examiner* — Nay A Maung
*Assistant Examiner* — Jose M Torres
(74) *Attorney, Agent, or Firm* — Ladas & Parry LLP

(57) ABSTRACT

Disclosed is a method for calculating fractional flow reserve, comprising: collecting a pressure at the coronary artery inlet of heart by a blood pressure sensor in real-time, and storing a pressure value in a data linked table; obtaining an angiographic time according to the angiographic image, finding out the corresponding data from data queues based on time index using the angiographic time as an index value, screening out stable pressure waveforms during multiple cycles, and obtaining an average pressure Pa; and obtaining a length of the segment of blood vessel from angiographic images of the two body positions, and obtaining a blood flow velocity V; calculating a pressure drop $\Delta P$ for the segment of the
(Continued)

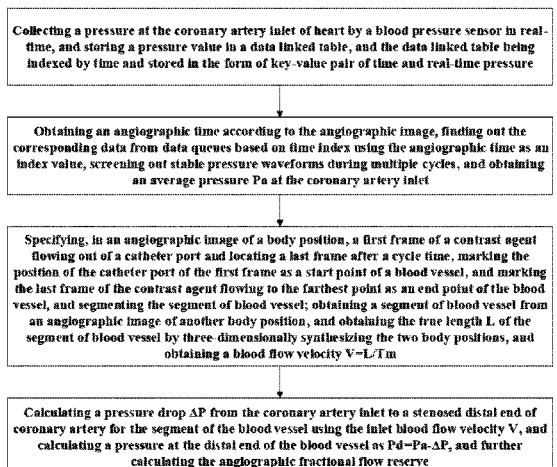

blood vessel using the blood flow velocity V at the coronary artery inlet, and calculating a pressure Pd at the distal end of the blood vessel, and further calculating the angiographic fractional flow reserve.

5 Claims, 1 Drawing Sheet

(51) Int. Cl.
  *A61B 5/0215* (2006.01)
  *A61B 5/107* (2006.01)
  *A61B 5/00* (2006.01)
  *G06T 7/00* (2017.01)
  *A61B 5/0275* (2006.01)
  *G06T 7/70* (2017.01)
  *A61M 31/00* (2006.01)

(52) U.S. Cl.
  CPC .......... *A61B 5/1075* (2013.01); *A61B 5/7278* (2013.01); *G06T 7/0012* (2013.01); *G06T 7/11* (2017.01); *G06T 7/70* (2017.01); *A61M 31/005* (2013.01); *G06T 2207/30104* (2013.01)

(58) Field of Classification Search
  CPC ... A61B 5/6869; A61B 5/1075; A61B 5/7278; A61B 6/481; G06T 7/0012; G06T 7/11; G06T 7/70; G06T 2207/30104; A61M 31/005
  See application file for complete search history.

(56) References Cited

U.S. PATENT DOCUMENTS

| | | | |
|---|---|---|---|
| 10,249,043 | B2 | 4/2019 | Ooga et al. |
| 10,342,442 | B2* | 7/2019 | Hattangadi .......... A61B 5/0215 |
| 10,398,386 | B2 | 9/2019 | Grady et al. |
| 10,993,628 | B2 | 5/2021 | Tochterman et al. |
| 11,031,136 | B2 | 6/2021 | Grass et al. |
| 11,064,897 | B2 | 7/2021 | Tu et al. |
| 11,087,884 | B2 | 8/2021 | Sankaran et al. |
| 2010/0222671 | A1* | 9/2010 | Cohen .................. G06V 40/103 600/424 |
| 2014/0276139 | A1* | 9/2014 | Burkett ................ A61B 5/6851 600/486 |
| 2018/0330507 | A1 | 11/2018 | Schormans et al. |
| 2019/0046125 | A1 | 2/2019 | Sharma et al. |
| 2019/0246918 | A1 | 8/2019 | Van den Brink |
| 2019/0380593 | A1 | 12/2019 | Bouwman et al. |
| 2021/0275124 | A1* | 9/2021 | Huo ........................ G16H 50/30 |
| 2021/0361176 | A1* | 11/2021 | Huo ..................... A61B 5/0275 |

FOREIGN PATENT DOCUMENTS

| | | |
|---|---|---|
| CN | 106327487 | 1/2017 |
| CN | 107730540 A | 2/2018 |
| CN | 107920764 | 4/2018 |
| CN | 108186038 | 6/2018 |
| CN | 108245178 | 7/2018 |
| CN | 108550189 | 9/2018 |
| CN | 108550388 | 9/2018 |
| CN | 109363651 | 2/2019 |
| JP | 2014113264 A | 6/2014 |
| JP | 2015097759 A | 5/2015 |
| JP | 2016511682 A | 4/2016 |
| JP | 2016135265 A | 7/2016 |
| JP | 2016537072 A | 12/2016 |
| JP | 2018061883 A | 4/2018 |
| JP | 2018533383 A | 11/2018 |
| JP | 2018535816 A | 12/2018 |
| JP | 2019524235 A | 9/2019 |
| WO | 2015138555 A2 | 9/2015 |

OTHER PUBLICATIONS

Japan Office Action for Application No. 2020-570502, dated Jan. 18, 2022.
Chinese Office Action dated Jan. 17, 2020 in respect of counterpart CN 201910206438.8.
Search Report dated Jan. 17, 2020 in respect of counterpart CN 201910206438.8.
Morris PD et al. Fast Virtual Fractional Flow Reserve Based Upon Steady-State Computational Fluid Dynamics Analysis: Results From the VIRTU—Fast Study. JACC Basic Transl Sci. Aug. 28, 2017;2(4):434-446.
Extended European Search Report for Application No. PCT/CN2019086610, dated Nov. 17, 2022, 5 pages.
ISR for International Application PCT/CN2019/086610, Dec. 2, 2019.
CN 106327487 A_English Abstract, Jan. 11, 2017.
CN 104582572 A_English Abstract, Apr. 29, 2015.
CN 107920764 A_English Abstract, Apr. 17, 2018.
CN 109363651 A_English Abstract, Feb. 22, 2019.
CN 108550189 A_English Abstract, Sep. 18, 2018.
CN108245178 A_English Abstract, Jul. 6, 2018.
CN 108186038 A_English Abstract, Jun. 22, 2018.
CN 105326486 A_English Abstract, Feb. 17, 2016.
CN 108550388 A_English Abstract Sep. 18, 2018.

* cited by examiner

```
┌─────────────────────────────────────────────────────────────────────────┐
│ Collecting a pressure at the coronary artery inlet of heart by a blood  │
│ pressure sensor in real-time, and storing a pressure value in a data    │
│ linked table, and the data linked table being indexed by time and       │
│ stored in the form of key-value pair of time and real-time pressure     │
└─────────────────────────────────────────────────────────────────────────┘
                                     │
                                     ▼
┌─────────────────────────────────────────────────────────────────────────┐
│ Obtaining an angiographic time according to the angiographic image,     │
│ finding out the corresponding data from data queues based on time index │
│ using the angiographic time as an index value, screening out stable     │
│ pressure waveforms during multiple cycles, and obtaining an average     │
│ pressure Pa at the coronary artery inlet                                │
└─────────────────────────────────────────────────────────────────────────┘
                                     │
                                     ▼
┌─────────────────────────────────────────────────────────────────────────┐
│ Specifying, in an angiographic image of a body position, a first frame  │
│ of a contrast agent flowing out of a catheter port and locating a last  │
│ frame after a cycle time, marking the position of the catheter port of  │
│ the first frame as a start point of a blood vessel, and marking the     │
│ last frame of the contrast agent flowing to the farthest point as an    │
│ end point of the blood vessel, and segmenting the segment of blood      │
│ vessel; obtaining a segment of blood vessel from an angiographic image  │
│ of another body position, and obtaining the true length L of the        │
│ segment of blood vessel by three-dimensionally synthesizing the two     │
│ body positions, and obtaining a blood flow velocity V=L/Tm              │
└─────────────────────────────────────────────────────────────────────────┘
                                     │
                                     ▼
┌─────────────────────────────────────────────────────────────────────────┐
│ Calculating a pressure drop ΔP from the coronary artery inlet to a      │
│ stenosed distal end of coronary artery for the segment of the blood     │
│ vessel using the inlet blood flow velocity V, and calculating a         │
│ pressure at the distal end of the blood vessel as Pd=Pa-ΔP, and further │
│ calculating the angiographic fractional flow reserve                    │
└─────────────────────────────────────────────────────────────────────────┘
```

METHOD FOR CALCULATING FRACTIONAL FLOW RESERVE BASED ON PRESSURE SENSOR AND ANGIOGRAPHIC IMAGE

CROSS-REFERENCE TO RELATED APPLICATION

This application is a continuation of International Application No. PCT/CN2019/086610, filed on May 13, 2019 which is based upon and claims priority to Chinese Patent Application No. 201910206438.8, filed on Mar. 19, 2019, the entire contents of which are hereby incorporated by reference.

TECHNICAL FIELD

The present disclosure relates to the field of coronary imaging evaluation, and in particular to, a method for calculating fractional flow reserve based on a pressure sensor and an angiographic image.

BACKGROUND

Fractional flow reserve (FFR) may indicate an influence of coronary stenosis lesion on distal blood flow and diagnose whether myocardial ischemia is present, and has become a recognized index of the functional assessment of the coronary stenosis. Many studies have proved the feasibility of an angiographic image and computational fluid dynamics to measure FFR.

The previous blood flow velocity measurement based on the frame counting method and the general manner for acquiring the inlet pressure Pa will cause errors of parameter collection, which makes the accuracy of the calculated FFR not high.

SUMMARY

In order to solve the above technical problems, an object of the present disclosure is to provide a method for calculating fractional flow reserve based on a pressure sensor and an angiographic image, which can accurately obtain the stable pressure value after the contrast agent is administrated, accurately obtain the average blood flow velocity within a cardiac cycle by the combination of a pressure waveform and an angiographic image, and can greatly improve the accuracy of FFR.

The technical solution of the present disclosure is to provide a method for calculating fractional flow reserve based on a pressure sensor and an angiographic image, comprising the following steps:

S01: collecting a pressure at the coronary artery inlet of heart by a blood pressure sensor in real-time, and storing a pressure value in a data linked table, and the data linked table being indexed by time and stored in the form of key-value pair of time and real-time pressure;

S02: obtaining an angiographic time according to the angiographic image, finding out the corresponding data from data queues based on time index using the angiographic time as an index value, screening out stable pressure waveforms during multiple cycles, and obtaining an average pressure Pa at the coronary artery inlet;

S03: specifying, in an angiographic image of a body position, a first frame of a contrast agent flowing out of a catheter port and locating a last frame after a cycle time, marking the position of the catheter port of the first frame as a start point of a blood vessel, and marking the last frame of the contrast agent flowing to the farthest point as an end point of the blood vessel, and segmenting the segment of blood vessel; obtaining a segment of blood vessel from an angiographic image of another body position, and obtaining the true length L of the segment of blood vessel by three-dimensionally synthesizing the two body positions, and obtaining a blood flow velocity $V=L/Tm$, wherein $Tm$ is a time for one cycle;

S04: calculating a pressure drop $\Delta P$ from the coronary artery inlet to a distal end of coronary artery for the segment of the blood vessel in step S03 using the inlet blood flow velocity V, and calculating a pressure at the distal end of the blood vessel as $Pd=Pa-\Delta P$, and further calculating the angiographic fractional flow reserve.

In the preferred technical solution, said step S01 further comprises: accumulating n points from the first point according to the time and real-time pressure value in the data linked table, obtaining a peak pressure value and a valley pressure value from the first point by comparison sort algorithm, continuously recording the peak pressure value and the valley pressure value to form a queue corresponding to the peak pressure value and the valley pressure value indexed by time, until completing the calculation of the nth point, and then sequentially taking next n points from the stored data finked table for calculation according to the time index, and so on.

In the preferred technical solution, in step S02, the average pressure Pa at the coronary artery inlet is calctuated by the systolic blood pressure and the diastolic blood pressure, and the average pressure=the diastolic blood pressure+(the systolic blood pressure−the diastolic blood pressure)/3.

In the preferred technical solution, a time interval from one peak pressure to the next peak pressure is calculated as a cycle, the average value of four peak pressure values is taken as the systolic blood pressure, the average value of four valley pressure values is taken as the diastolic blood pressure, and the average time Tm of the four cycles is taken as the time of one cycle.

In the preferred technical solution, the stable pressure waveforms in step S02 is waveforms in which the relative difference of peak values of the waveforms during successive multiple cycles is within 4 mmHg.

Compared with the prior art, the advantages of the present disclosure comprise accurately obtaining the stable pressure value after administrating the contrast agent, accurately obtaining the average blood flow velocity within a cardiac cycle by the combination of a pressure waveform and an angiographic image, and greatly improving the accuracy of FFR.

BRIEF DESCRIPTION OF DRAWINGS

The present disclosure will be further described below with reference to the drawings and embodiments.

FIG. 1 is a flow chart of a method for calculating fractional flow reserve based on a pressure sensor and an angiographic image according to the present disclosure.

DETAILED DESCRIPTION OF PREFERRED EMBODIMENTS

In order to make the purposes, technical solutions and advantages of the disclosure clearer, the present disclosure will be described in detail below in conjunction with the specific embodiments and the corresponding accompanying drawings. It should be understood that these descriptions are only exemplary and are not intended to limit the scope of the present disclosure. In addition, in the following description, descriptions of well-known structures and technologies are omitted to avoid unnecessary confusion of the concept of the present disclosure.

As shown in FIG. 1, a method for calculating fractional flow reserve based on a pressure sensor and an angiographic image according to the present disclosure comprises the following steps:

1. collecting a pressure at the coronary artery inlet of heart by a blood pressure sensor in real-time, the pressure sensor communicating with the aorta through a pressure tube and a surgical catheter to keep the pressure sensor at the same level as the heart.

2. sensing pressure fluctuations and generating an electrical signal by a pressure chip of the pressure sensor, transmitting the signal to the acquisition chip of a control unit through a cable, and converting the electrical signal by the acquisition chip into a pressure value and filtering it to form a stable pressure waveform.

3. storing a pressure value in a data linked table by a data processing chip of the control unit, and the data linked table being indexed by time and stored in the form of key-value pairs of time and real-time pressure.

4. accumulating n points from the first point according to the time and real-time pressure value in the data linked table by the data processing chip in which the number of n is the position when passing at least 4 seconds from the first point according to the time index and is above about 4 cardiac cycles; obtaining a peak pressure value and a valley pressure value from the first point by comparison sort algorithm, continuously recording the peak pressure value and the valley pressure value to form a queue corresponding to the peak pressure value and the valley pressure value indexed by time, until completing the calculation of the nth point, and then sequentially taking next n points from the stored data linked table for calculation according to the time index, and so on.

5. further calculating the systolic blood pressure, the diastolic blood pressure and heart rate from the data queues stored in step 4, calculating pressure values from one peak to the next peak as a cycle, taking the average value of four peak pressure values as the systolic blood pressure, taking the average value of four valley pressure values as the diastolic blood pressure, calculating the heart rate using the average time Tm of the four cycles, the heart rate=60/Tm. Parameters such as the systolic blood pressure, the diastolic blood pressure, the average pressure and the heart rate can be obtained so as to provide more accurate data for the next steps.

6. obtaining the pressure of the angiographic blood vessel in order to calculate FFR, in which, first, obtaining an angiographic time from angiographic images, finding out the corresponding data from the data queues in step 4 according to the time index using the angiographic time as the index value, and then screening out stable pressure waveforms during 4 cycles from this data in which the criterion for stable pressure is that the relative difference of peak values of the waveforms during successive 4 multiple cycles is within 4 mmHg; obtaining a stable systolic blood pressure, diastolic blood pressure and heart rate based on the method of step 5; calculating the average pressure Pa at the coronary artery inlet from the systolic blood pressure and the diastolic blood pressure by the formula: the average pressure=the diastolic blood pressure+(the systolic blood pressure−the diastolic blood pressure)/3. Since the bolus injection of the contrast agent at the time of angiograph will cause the pressure fluctuation to disappear, the stable value for recovery of the pressure fluctuation can be accurately obtained after cease of the bolus injection of the contrast agent according to the periodic data queues continuously recorded in step 4. This ensures that the acquired patient pressure physiological parameters are the parameters corresponding to the time of angiograph.

7. using the heart rate and the time Tm for one cycle obtained in step 6 when calculating the flow velocity, specifying, in an angiographic image, a first frame of a contrast agent flowing out of a catheter port and locating a last frame after a cycle time, marking the position of the catheter port of the first frame as a start point of a blood vessel, and marking the last frame of the contrast agent flowing to the farthest point as an end point of the blood vessel, and segmenting the segment of blood vessel; equally obtaining a segment of blood vessel from an angiographic image of another body position, and obtaining the true length L of the segment of blood vessel by three-dimensionally synthesizing the two body positions, and obtaining a blood flow velocity V=L/Tm. This ensures that the average blood flow velocity within a cardiac cycle can be accurately obtained when calculating the flow velocity. For the specific three-dimensional synthesis method, please refer to the Chinese patent document with an application number of 201610681191.1, which will not be repeated here in the present invention.

8. Obtaining $\Delta P$ of a segment of blood vessel in step 7 calculated by the inlet blood flow velocity V through computational fluid dynamics, wherein $\Delta P$ is a pressure drop from the coronary artery inlet to a distal end of coronary artery, obtaining a pressure Pa at the inlet of blood vessel in step 6, calculating a pressure at the distal end of the blood vessel as Pd=Pa−$\Delta P$, and obtaining the angiographic fractional flow reserve by calculating according to the angiographic fractional flow reserve formula FFR=Pd/Pa.

For the specific calculation methods of $\Delta P$, please refer to the calculation of $\Delta P$ in Chinese patent document with an application number of 201610681191.1. The present disclosure will not repeat them here.

It should be understood that the specific embodiments mentioned above are merely intended to exemplify or explain of the principles of the present disclosure and not to be limitations to the present disclosure. Therefore, any modifications, equivalent substitutions, improvements and the like made without departing from the spirit and scope of the present disclosure should be included in the protection scope of the present disclosure. In addition, the appended claims of the present disclosure are intended to cover all changes and modifications falling within the scope and boundary of the appended claims, or equivalents of such scope and boundary.

What is claimed is:

1. A method for calculating fractional flow reserve based on a pressure sensor and an angiographic image, characterized in that, comprising the following steps:

S01: collecting a pressure at the coronary artery inlet of heart by a blood pressure sensor in real-time, and storing a pressure value in a data linked table, and the data linked table being indexed by time and stored in the form of key-value pair of time and real-time pressure;

S02: obtaining an angiographic time according to the angiographic image, finding out the real-time pressure corresponding to the angiographic time from data queues based on time index using the angiographic time as an index value, screening out stable pressure waveforms during multiple cardiac cycles, and obtaining an average pressure Pa at the coronary artery inlet, wherein the stable pressure waveforms are waveforms in which the relative difference of peak values of the waveforms during successive multiple cardiac cycles is within a predetermined threshold, and the average pressure Pa at the coronary artery inlet is calculated by the systolic blood pressure and the diastolic blood pressure, wherein a time interval from one peak pressure value to the next peak pressure value is calculated as a cardiac cycle, the average value of multiple peak pressure values is taken as the systolic blood pressure, the average value of multiple valley pressure values is taken as the diastolic blood pressure, and the average time Tm of multiple cardiac cycles is taken as the time of one cardiac cycle;

S03: specifying, in an angiographic image of a first body position, a first frame of a contrast agent flowing out of a catheter port and locating a last frame after a cardiac cycle time, marking the position of the catheter port of the first frame as a start point of a blood vessel, and marking the last frame of the contrast agent flowing to the farthest point as an end point of the blood vessel, and segmenting the segment of blood vessel which is from the position of the catheter port to the farthest point of the contrast agent flowing; obtaining a segment of blood vessel which is from the position of the catheter port to the farthest point of the contrast agent flowing from an angiographic image of a second body position, and obtaining the true length L of the segment of blood vessel by three-dimensionally synthesizing the angiographic image of the first body position and the angiographic image of the second body position, and obtaining a blood flow velocity V=L/Tm, wherein Tm is a time for one cardiac cycle;

S04: calculating a pressure drop $\Delta P$ from the coronary artery inlet to a distal end of coronary artery for the segment of the blood vessel which is from the position of the catheter port to the farthest point of the contrast agent flowing in step S03 using the inlet blood flow velocity V through computational fluid dynamics, and calculating a pressure at the distal end of the blood vessel as Pd=Pa−$\Delta P$, and further calculating the angiographic fractional flow reserve according to the angiographic fractional flow reserve formula FFR=Pd/Pa.

2. The method for calculating fractional flow reserve based on the pressure sensor and the angiographic image according to claim 1, wherein said step S01 further comprises: accumulating n points from the first point according to the time and real-time pressure value in the data linked table, obtaining a peak pressure value and a valley pressure value from the first point by comparison sort algorithm, continuously recording the peak pressure value and the valley pressure value to form a queue corresponding to the peak pressure value and the valley pressure value indexed by time, until completing the calculation of the nth point, and then sequentially taking next n points from the stored data linked table for calculation according to the time index, and so on, wherein the number of n is the position when passing at least 4 seconds from the first point according to the time index and is above about 4 cardiac cycles.

3. The method for calculating fractional flow reserve based on the pressure sensor and the angiographic image according to claim 1, wherein in step S02, the average pressure=the diastolic blood pressure+(the systolic blood pressure−the diastolic blood pressure)/3.

4. The method for calculating fractional flow reserve based on a pressure sensor and an angiographic image according to claim 3, wherein the average value of four peak pressure values is taken as the systolic blood pressure, the average value of four valley pressure values is taken as the diastolic blood pressure, and the average time Tm of the four cycles is taken as the time of one cycle.

5. The method for calculating fractional flow reserve based on the pressure sensor and the angiographic image according to claim 1, wherein the stable pressure waveforms in step S02 is waveforms in which the relative difference of peak values of the waveforms during successive multiple cycles is within 4 mmHg.

* * * * *